(12) United States Patent
Jin et al.

(10) Patent No.: US 10,101,245 B2
(45) Date of Patent: Oct. 16, 2018

(54) SUBSAMPLING DEVICE AND METHOD

(71) Applicant: NATIONAL INSTITUTE OF ADVANCED INDUSTRIAL SCIENCE AND TECHNOLOGY, Tokyo (JP)

(72) Inventors: Yusuke Jin, Sapporo (JP); Yoshihiro Konno, Sapporo (JP); Jiro Nagao, Sapporo (JP)

(73) Assignee: NATIONAL INSTITUTE OF ADVANCED INDUSTRIAL SCIENCE AND TECHNOLOGY, Tokyo (JP)

( * ) Notice: Subject to any disclaimer, the term of this patent is extended or adjusted under 35 U.S.C. 154(b) by 312 days.

(21) Appl. No.: 15/100,400

(22) PCT Filed: Dec. 4, 2014

(86) PCT No.: PCT/JP2014/082087
§ 371 (c)(1),
(2) Date: May 31, 2016

(87) PCT Pub. No.: WO2015/087767
PCT Pub. Date: Jun. 18, 2015

(65) Prior Publication Data
US 2016/0299040 A1    Oct. 13, 2016

(30) Foreign Application Priority Data
Dec. 9, 2013   (JP) .................................. 2013-254505

(51) Int. Cl.
*G01N 1/08*      (2006.01)
*E02D 1/04*      (2006.01)
*G01N 1/10*      (2006.01)

(52) U.S. Cl.
CPC ................. *G01N 1/08* (2013.01); *E02D 1/04* (2013.01); *G01N 2001/105* (2013.01); *G01N 2001/1037* (2013.01)

(58) Field of Classification Search
CPC ......... G01N 1/08; E21B 25/005; E21B 49/02; E21B 49/06; E02D 1/04
See application file for complete search history.

(56) References Cited

U.S. PATENT DOCUMENTS 4,376,392 A * 3/1983 Beitel ...................... E02D 1/04
                                                             73/864.45
4,625,813 A    12/1986 Trivedi et al.

FOREIGN PATENT DOCUMENTS

DE    102005006039 A1    8/2006
JP    2002-059295 A    2/2002
(Continued)

OTHER PUBLICATIONS

Supplementary European Search Report dated Nov. 16, 2016 for related European Patent Application No. 14868823.7.
(Continued)

*Primary Examiner* — Paul West
(74) *Attorney, Agent, or Firm* — Enshan Hong; VLP Law Group LLP

(57) ABSTRACT

A subsampling device comprising a flange member in which a through hole to be in communication with a housing space of a sample storing container is formed; a coupling member in which a cavity to be in communication with the through hole of the flange member is formed; a cylindrical casing which has a front end connected to a second end of the coupling member; a sampling pipe; and a sample container which is replaceable with the flange member, and which is connected to the first end of the coupling member, in which the sliding sampling pipe causes the collecting blade to contact a sample in the sample storing container to perform
(Continued)

subsampling on the sample so as to be held at the front end of the sampling pipe, and the sample having undergone the subsampling is stored in the attached sample container replaced with the flange member.

7 Claims, 20 Drawing Sheets

(56) References Cited

FOREIGN PATENT DOCUMENTS

| JP | 3106269 U | 12/2004 |
|---|---|---|
| JP | 2005-298745 A | 10/2005 |
| JP | 2008-046083 A | 2/2006 |
| JP | 2007-262271 A | 10/2007 |
| JP | 2012-046696 A | 3/2012 |

OTHER PUBLICATIONS

R. John Parkes et al.: "Cultrualable prokaryotic diversity of deep, gas hydrate sediments: first use of a continuous high-pressure, anaerobic, enrichment and isolation system for subseafloor sediments (Deep I soBUG)", Environmental Microbiology, vol. 11, No. 12 (Dec. 1, 2009), pp. 3140-3153, ISSN:1462-2912, DOI:10.1111/i.1462-2920.2009.02108.x.

E. Dendy Sloan et al., Clathrate Hydrates of Natural Gases, Third Edition, (2007).

J. Carlos Santamarina et al., Pressure Core Characterization Tools for Hydrate-Bearing Sediments, Scientific Drilling, No. 14, Sep. 2012, pp. 44-48.

Peter Schultheiss et al.,Wireline Coring and Analysis under Pressure: Recent Use and Future Developments of the HYACINTH System, Scientific Drilling, No. 7, Mar. 2009, pp. 44-50.

Yusuke Jin et al., New Method of Assessing Absolute Permeability of Natural Methane Hydrate Sediments by Microfocus X-ray Computed Tomography, Japanese Journal of Applied Physics, vol. 46, No. 5A, 2007, pp. 3159-3162.

Peter Schultheiss et al., PCATS:Pressure core analysis and transfer system, Proceedings of the 7th International Conference on Gas Hydrates, 2011.

Satoshi Kubo, Tokuhiro Inada, "Dai 1 Kai Kaiyo Sanshutsu Shiken Kaiyo Sanshutsu Shiken Chiiki no Choryuso Hyoka Atsuryoku Core no Shutoku Sagyo to Jisseki", JOGMEC Sekiyu Kaihatsu Gijutsu Honbu Nenpo, Aug. 30, 2013 (Aug. 30, 2013), vol. 2012, pp. 201 to 203.

* cited by examiner (a)

(b) 
160e (a)

(b)

(a)

(b)

(c)

SUBSAMPLING DEVICE AND METHOD

PRIORITY CLAIM

This is a U.S. national stage of application No. PCT/JP2014/082087, filed on Dec. 4, 2014. Priority is claimed on the following applications: Country: Japan, Application No.: 2013-254505, Filed: Dec. 9, 2013, the content of which is incorporated here by reference

TECHNICAL FIELD

The present disclosure relates to a subsampling device and method.

BACKGROUND ART

Gas hydrate is a stable solid crystal under a low-temperature and a high-pressure condition in which gas molecules are contained in a cage-shape structure formed by water molecules.

Gas hydrate is capable of containing substantially 170 m$^3$ gas molecules per a volume of 1 m$^3$. Hence, gas hydrate is also studied and developed as a transporting and storing medium of natural gas (see Patent Literatures 1-3 and Non-Patent Literature 1).

In recent years, presentation of gas hydrate (hereinafter, referred to as natural gas hydrate) containing methane molecules as a primary component in permanently frozen grounds and deposit layers at sea bottoms have been confirmed (see Non-Patent Literature 1). In addition, a large amount of natural gas hydrate present in deposits in the sea around Japan has also been confirmed, and a development as a non-conventional energy resource to replace petroleum oil and coal is advancing.

An example researching method for natural gas hydrate is a so-called seismic method of causing vibrations (sonic waves) like earthquakes, and checking the reflection speed from deposit layers, and the distributed condition of natural gas hydrate present in the natural world has been researched through such a method.

In addition, excavation of deposit layers and inspection of the amount of resources and necessary physical properties for gas productivity evaluation using various sensors have been carried out. Still further, target deposit layers are collected, and the physical properties of the deposit sample of natural gas hydrate is researched. This enables a highly precise evaluation of the amount of resources and the gas productivity.

Several reports have been made for such methods of collecting deposit samples.

Patent Literature 4 discloses a scheme of performing sampling on, for example, pore water in deposits and microorganisms contained therein while maintaining the condition of the geological layer.

Meanwhile, gas hydrate is stably present under a low-temperature and a high-pressure condition, but when the condition becomes a temperature and a pressure condition out of the phase-stable temperature and pressure range of gas hydrate due to a temperature rise and a pressure reduction, hydrate will decompose. Hence, several schemes of collecting and analyzing a deposit sample containing gas hydrate so as not to allow gas hydrate decompose have been reported.

Non-Patent Literature 2 discloses, for a deposit sample collected with the temperature and the pressure being maintained, a method of performing a saturation factor measurement, a thermal conductivity measurement, a mechanistic responsiveness measurement of hydrate contained in the deposit sample, and of collecting the pore water in deposits. According to this method, with a deposit sample protected by a liner having undergone a coring being as a target, for example, an opening is formed in the liner to allow an analyzer device to contact the sample, thereby performing an analysis in a pressurized container (in general, the collected deposit is covered and protected by a plastic liner so as not to apply shock to the deposit at the time of coring). According to this method, after the sample is collected, evaluation of the physical properties of the deposit is enabled in the pressurized container without causing the gas hydrate in the deposit to decompose while maintaining the pressure.

In addition, Non-Patent Literature 3 discloses a method of collecting a deposit sample that has been collected with the temperature and the pressure being maintained, and producing a sample piece for analysis. According to this method, a gas hydrate deposit sample is pushed out as a cylindrical column in the axial direction, is cut in a desired length using a ball valve, and is kept in another pressurized container.

Still further, the ratio in volume between sands forming the deposit layer and materials other than sand (hereinafter, referred to as a porosity) is strongly associated with the permeability of gas and that of water, and an example method for measuring the porosity of the deposit is generally to first let the deposit dry, and then to measure the volume and weight of the dried deposit (hereinafter, referred to as a drying method). Since the deposit layer containing gas hydrate is formed of unconsolidated sands, however, according to the drying method of utilizing the dried sample that has gas hydrate decomposed, sands are moved due to the decomposition of hydrate, the layout of sand grains becomes different from the condition in which the sample was present in the geological layer, and the sample that contains more gas hydrate in the pores is more likely to change the volume since the layout of sands changes due to the produced decomposed gas. In addition to the drying method, a method of making the pores in a deposit visible through an X-ray computed tomography (CT) method and a synchrotron CT method, and calculating the porosity is also known (hereinafter, referred to as a CT method). According to conventional CT methods, however, since the deposit containing gas hydrate is once released to an ambient pressure, and the gas hydrate is thus decomposed, there is a problem that the layout of sands changes. As explained above, according to conventional drying and CT methods, precise evaluation of the gas productivity is quite difficult.

Hence, a method of measuring the porosity regardless of the conventional drying and CT methods has been reported. Non-Patent Literature 4 discloses to release a gas hydrate deposit having the pressure maintained to an ambient pressure, to quickly freeze the gas hydrate deposit using a liquid nitrogen, and to perform an X-ray CT imaging on the frozen sample, thereby measuring the porosity in a non-destructive manner.

CITATION LIST

Patent Literature

Patent Literature 1: Unexamined Japanese Patent Application Kokai Publication No. 2012-46696
Patent Literature 2: Unexamined Japanese Patent Application Kokai Publication No. 2007-262271
Patent Literature 3: Unexamined Japanese Patent Application Kokai Publication No. 2005-298745

Patent Literature 4: Unexamined Japanese Patent Application Kokai Publication no. 2008-46083

Non Patent Literature

Non Patent Literature 1: Sloan, E. D. and Koh, C. A: Clathrate Hydrates of Natural Gases, Third Edition (2007)
Non Patent Literature 2: Santamarina, J. C., Dai, S., Jang, J., and Terzariol, M. Scientific Drilling, No. 14, September 2012, 44-48
Non Patent Literature 3: Schultheiss, P., Holland, M., Humphrey, G. Scientific Drilling, 7, 44-50, 2009
Non Patent Literature 4: Jin, Y., Hayashi, J., Nagao, J., Suzuki, K., Minagawa, H., Ebinuma, T., and Narita H. Japanese Journal of Applied Physics Part 1, vol. 46 (5A), pp. 3159-3162, 2007. 5

SUMMARY OF INVENTION

Technical Problem

According to the method disclosed in Patent Literature 4, however, sampling is not performed while maintaining the pressure, and when sampling is performed on the gas hydrate deposit by the method disclosed in Patent Literature 4, the gas hydrate deposit needs to first be released to an ambient pressure, and then to be frozen. Hence, a problem that gas hydrate is decomposed still remains.

In addition, according to the method disclosed in Non-Patent Literature 2, analysis is performed using a circular columnar sample with a diameter of substantially 5 cm, and thus evaluation of the gas hydrate condition present in the pores among fine sand grains in a micro order in the deposit is difficult.

Still further, according to the method disclosed in Non-Patent Literature 3, although subsampling on the sample is possible while maintaining the pressure, this method is to push out and collect a soft muddy deposit layer. Hence, application of this method for sampling a solid sand deposit layer is difficult. In addition, in a process of sealing the sample having undergone subsampling in a pressurized container, a vast and heavy ball valve is applied. Hence, there is a problem in practice for an actual analysis site. In addition, since the sample is cut by the ball valve, a change in physical properties due to an application of mechanical shock is a concern.

Yet still further, according to the method disclosed in Non-Patent Literature 4, since the sample is frozen by a liquid nitrogen, the pores are expanded due to the frozen pore water, and the layout of sand grains becomes different from a condition in which the sample was present in the geological layer. Moreover, there is another problem that the smaller the amount of contained gas hydrate is, the more the adverse effect originating from the expansion of frozen water becomes (this is because the smaller the amount of contained gas hydrate is, the larger the amount of pore water becomes). Also, gas hydrate is decomposed when the sample is released to an ambient pressure. In this case, not only the amount of pore water changes due to the production of water originating from decomposition, but also how much of the gas hydrate is decomposed is unmeasurable. Hence, a correction on the porosity in consideration of the water expansion is difficult.

The present disclosure has been made in view of the foregoing circumstances, and an objective of the present disclosure is to provide a subsampling device and method for a sample while maintaining a predetermined pressure.

Solution to Problem

In order to accomplish the above objective, a subsampling device according to a first aspect of the present disclosure includes:
a flange in which a through hole to be in communication with a housing space of a sample storing container is formed, and which is formed with at least one first pressure adjusting passage in communication with the through hole, and which is coupled to a rear end face of the sample storing container;
a coupling member in which a cavity to be in communication with the through hole of the flange member is formed, and which has a first end coupled to the through hole of the flange member;
a cylindrical casing which has a front end connected to a second end of the coupling member, includes a ball valve disposed at a nearby location to the front end, and formed with at least one second pressure adjusting passage formed at a nearby location to a rear end of the cylindrical casing and in communication with an internal space thereof;
a sampling pipe which is provided with a partition wall that divides the internal space into a front space and a rear space, includes a collecting blade formed at a front end, and slides in the internal space of the cylindrical casing; and
a sample container which is replaceable with the flange member, and which is connected to the first end of the coupling member,
in which the sliding sampling pipe causes the collecting blade to contact a sample in the sample storing container to perform subsampling on the sample so as to be held at the front end of the sampling pipe, and the sample having undergone the subsampling is stored in the attached sample container replaced with the flange member.

The sampling pipe slides by, for example, a pressure difference between the front space and the rear space.

The coupling member includes, for example, at least one third pressure adjusting passage in communication with the cavity.

The second pressure adjusting passage is connected to, for example, an external pressure adjusting mechanism, and produces the pressure difference between the front space and the rear space by the pressure adjusting mechanism.

The subsampling device further includes, for example, a push-out member which protrudes from the front end of the sampling pipe, and which causes the sample to be housed in the sample container.

For example, an open end of the sample container is sealed after the sample is housed therein.

The subsampling device further includes, instead of the sampling pipe, a plug and a plug rod member.

A subsampling method for a sample according to a second aspect of the present disclosure includes:
a process of causing a sampling pipe to slide along an axial line direction by a pressure difference between a front space and a rear space relative to the sampling pipe, causing a collecting blade of the sampling pipe to contact the sample in a sample storing container to collect the sample;
a process of taking out the sample storing container and a flange member from a device main body and attaching a sample container to a coupling member;
a process of housing the collected sample held at a tip of the sampling pipe in the sample container; and sealing an open end of the sample container housing therein the sample.

Advantageous Effects of Invention

According to the present disclosure, subsampling device and method for a sample while maintaining a predetermined pressure are provided.

BRIEF DESCRIPTION OF DRAWINGS

FIG. 1A is a partial cross-sectional view illustrating a condition in which the tip of a sampling pipe is located behind a ball valve, while FIG. 1B is a partial cross-sectional view illustrating a condition in which the tip of the sampling pipe reaches a sample;

FIG. 3A is a perspective view illustrating a condition in which a collecting blade is protruding, while FIG. 3B is a perspective view illustrating a condition in which a push-out member is further protruding;

DESCRIPTION OF EMBODIMENTS

An embodiment of the present disclosure will be explained below in detail.

Figure 1A:
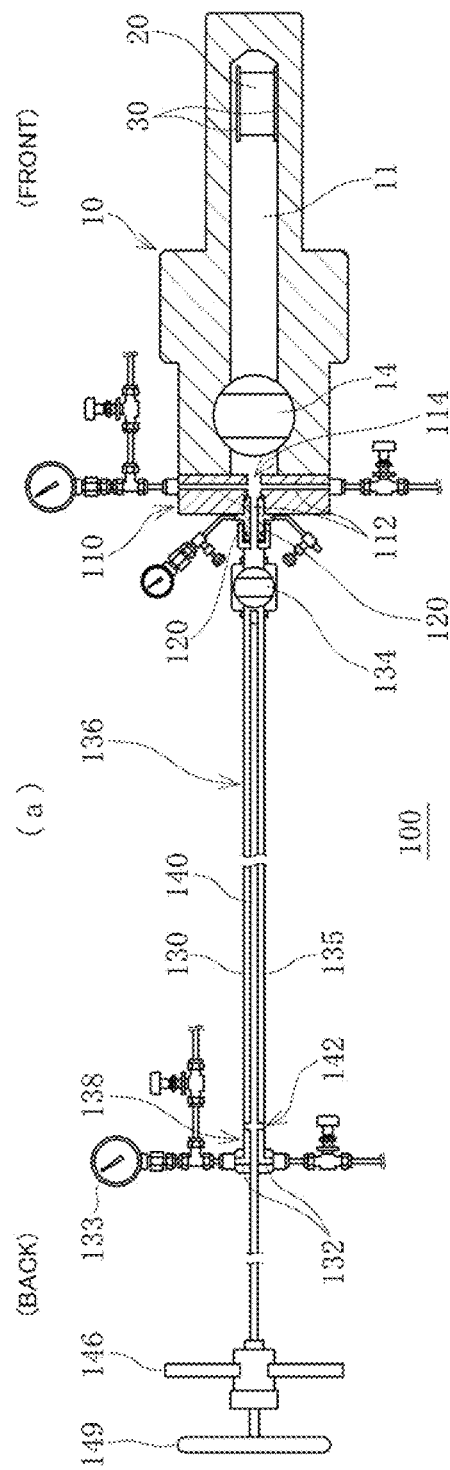
FIGS. 1A and 1B are each a partial cross-sectional view illustrating exemplary entire and internal structures of a subsampling device according to an embodiment of the present disclosure.
Figure 1B:
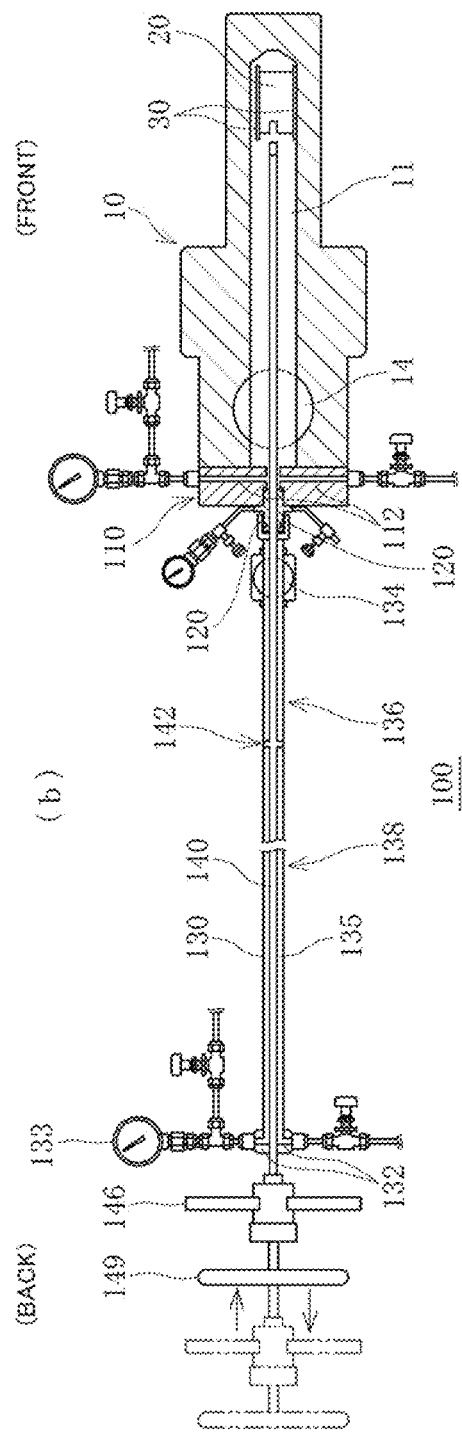

FIGS. 1A and 1B are each a partial cross-sectional view illustrating exemplary entire and internal structures of a subsampling device 100 according to an embodiment of the present disclosure. A structure of the subsampling device will be explained below with reference to those figures.

In this specification, the term "subsampling" means, using a sample collected (sampling) from a deposit layer or the like, to collect a further smaller amount of sample from the former sample, and to produce a sample piece for analysis.

As illustrated in FIGS. 1A and 1B, the subsampling device 100 according to an embodiment of the present disclosure includes a flange member 110 that is coupled to an end face of a conventionally well-known sample storing container 10, a coupling member 120 that is to connect a cylindrical casing 130 to a rear end face of the flange member 110, the cylindrical casing 130, and a sampling pipe 140 which is housed in the cylindrical casing 130 in a freely slidable manner thereinside, and which performs subsampling.

In this specification, the back-and-forth direction of the subsampling device 100 is as illustrated in FIGS. 1A and 1B.

The flange member 110 is formed in a thick disk shape that has the same diameter as that of the conventionally well-known sample storing container 10 available from GEOTEK corporation, and as illustrated in FIGS. 1A and 1B, is coupled to the rear end face of the sample storing container 10 by bolts (unillustrated). The sample storing container 10 is a container that is capable of storing a deposit sample 20 containing gas hydrate and collected from deposit layers at the front end side in a housing space 11 formed in the sample storing container. In addition, by opening and closing a ball valve 14 provided at the rear end side of the housing space 11, the internal pressure of the sample storing container 10 can be released to and maintained.

A through hole 114 that can be in communication with the interior of the sample storing container 10 is formed in the circular center of the flange member 110. A female screw (unillustrated) to be screwed with a front male screw 120a of the coupling member 120 to be explained later is formed on an inner circumference of the through hole 114. In addition, the flange member 110 includes two first piping paths (first pressure adjusting passage) 112 which are formed so as to intersect at a right angle with the axial line of the through hole 114, and which are in communication with the through hole 114. The first piping paths 112 are connected to a syringe pump (pressure adjusting mechanism) to be explained later.

Figure 2:
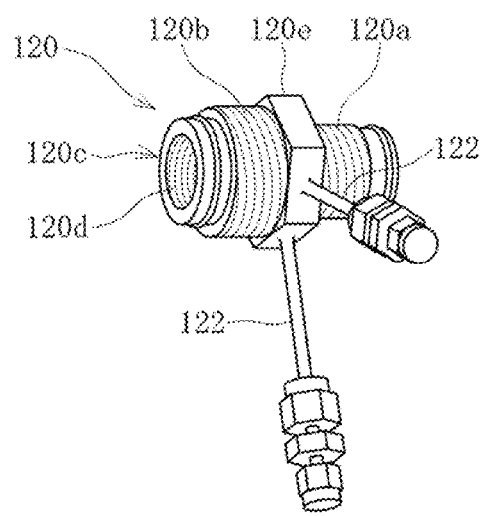
FIG. 2 is a perspective view illustrating an exemplary coupling member.

As illustrated in FIG. 2, the coupling member 120 is formed in a cylindrical shape, the front male screw 120a to be screwed with the female screw (unillustrated) of the through hole 114 of the flange member 110 is formed at the front side relative to a center flange 120e, and a rear male screw 120b to be screwed with a female screw (unillustrated) formed inwardly at the front end of the cylindrical casing 130 to be explained later is formed at the rear side. In addition, a cavity 120c to be in communication with the through hole 114 of the flange member 110 is formed in the coupling member 120. The one end (front side) of the coupling member 120 is caused to be in communication with the through hole 114 of the flange member 110 by the front male screw 120 that is screwed with the female screw (unillustrated) of the through hole 114 of the flange member 110. Still further, the center flange 120e of the coupling member 120 is connected to two third pipes (third pressure adjusting passage) in communication with the cavity 120c.

The cylindrical casing 130 has an internal space 135 thereinside, and as illustrated in FIGS. 1A and 1B, has the front end connected to the rear end face of the coupling member 120. The cylindrical casing 130 is coupled to the coupling member 120 by the female screw (unillustrated) at the front end of the cylindrical casing 130 which is screwed with the rear male screw 120b of the coupling member 120. A ball valve 134 is provided at the nearby location to the front end of the cylindrical casing 130, and two second piping paths (second pressure adjusting passage) 132 which are in communication with the internal space 135 are formed at the nearby location to the rear end of the cylindrical casing 130. The second piping paths 132 are connected to a supply pipe from the syringe pump (pressure adjusting mechanism) to be explained later.

Figure 3A:
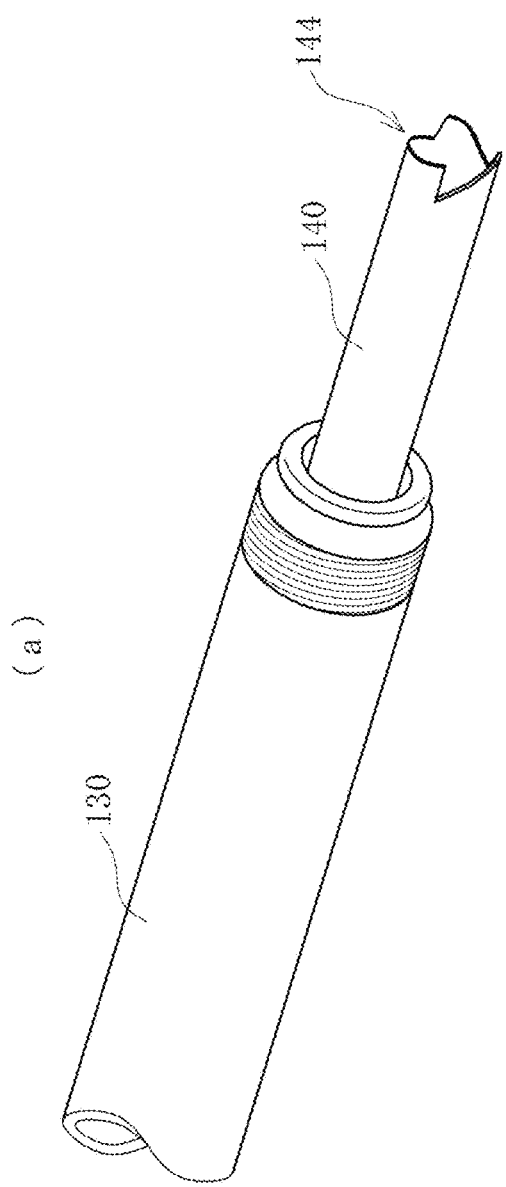
FIGS. 3A and 3B are perspective views illustrating an exemplary tip portion of the sampling pipe.

As illustrated in FIGS. 1A and 1B, the sampling pipe 140 is a thin and elongated circular tube member, and is slidable in the internal space 135 of the cylindrical casing 130. A collecting blade 144 (see FIG. 3A) is provided at the front end of the sampling pipe 140. Subsampling is performed on the sample 20 using this collecting blade 144 (see FIG. 1B). The collecting blade 144 is formed so as to form the tip tubular wall of the sampling pipe 140 in a saw-edge shape (see FIG. 3A). The collected sample 20 can be housed in the tip portion of the sampling pipe 140 using this collecting blade 144. In addition, as illustrated in FIGS. 1A and 1B, the sampling pipe 140 includes a disk-shape bulk head (partition wall) 142 that divides the internal space 135 of the cylindrical casing 130 into a front space 136 and a rear space 138. An O-ring (unillustrated) is attached to the inner circumference of the bulk head 142 so as to accomplish smooth sliding inside the cylindrical casing 130. As will be explained later, the bulk head 142 is provided so as to produce a pressure difference between the front space 136 and the rear space 138. In addition, when the sampling pipe 140 is not actuated, the bulk head 142 abuts the internal side of the cylindrical casing 130, and when the sampling pipe 140 is actuated back and forth, the bulk head 142 is slidable back and forth in the cylindrical casing 130. In addition, a handle 146 that reciprocates the sampling pipe 140 in the back-and-forth direction is attached to the rear end of the sampling pipe 140 (see FIGS. 1A and 1B).

Figure 3B:
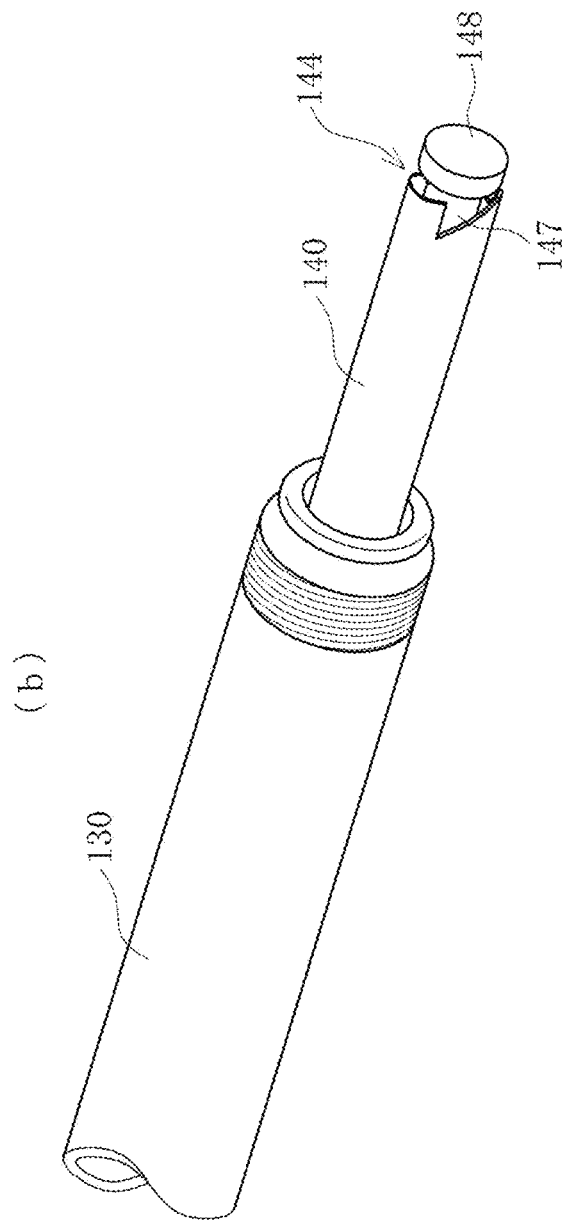

As illustrated in FIG. 3B, a push-out member 148 that pushes out the sample 20 collected by the collecting blade 144 and housed in the tip of the sampling pipe 140 to the interior of a sample container 150 (which will be explained later) is provided at the front end of the sampling pipe 140. The push-out member 148 is formed in a disk shape, and is connected to a push-out handle 149 (see FIGS. 1A and 1B) attached to the rear end of the sampling pipe 140 through a shaft member 147 (see FIG. 3B) inside the sampling pipe 140. When the push-out handle 149 is pushed forward the push-out member 148 is actuated in the forward direction, and thus the sample 20 housed in the collecting blade 144 can be pushed out to the interior of the sample container 150 (which will be explained later).

In this case, an explanation will be given of an operation of transferring the sample 20 having undergone subsampling from the sample storing container 10 with reference to FIGS. 4A-7E. In order to transfer the sample 20 having undergone subsampling from the sample storing container 10, the sample container 150 (see FIG. 4A), a plug 160 (see FIG. 5A), and a plug rod member 170 (see FIG. 7E) are newly applied.

Figure 4A:
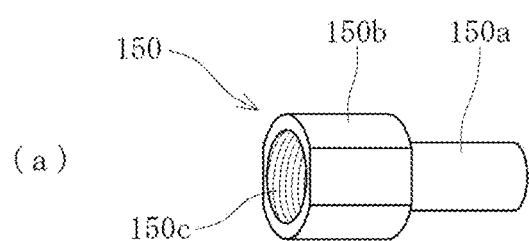
FIG. 4A is a perspective view illustrating an exemplary sample container.
Figure 4B:
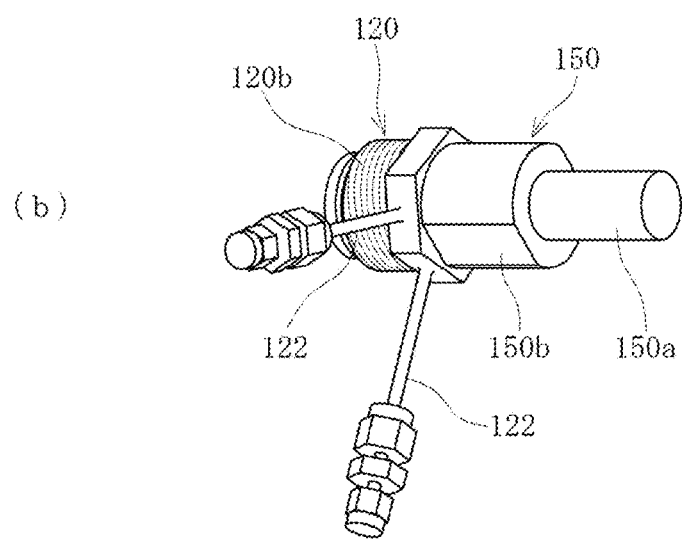
FIG. 4B is a perspective view illustrating an exemplary coupling condition between the coupling member and the sample container.

The sample container 150 is a container for keeping and analyzing the transferred sample 20 from the sample storing container 10. The sample container 150 according to this embodiment is formed of duralumin AA2024, and has a thickness of 1.5 mm in consideration of an X-ray intensity and a pressure tightness so as to be applicable to an X-ray CT analysis. As illustrated in FIG. 4A, the front side of the sample container 150 is a cylindrical keeper portion 150a, while the rear side is a coupler portion 150b that has a larger diameter than that of the keeper portion 150a. A female screw 150c is formed in the coupler portion 150b, and is screwed with the front male screw 120a of the coupling member 120, thereby causing the coupling member 120 to be coupled to the sample container 150 (see FIG. 4B).

Figure 5A:
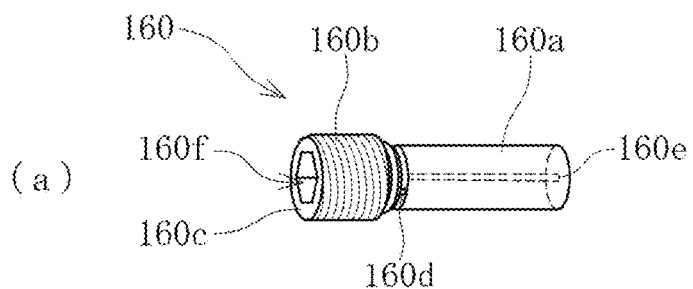
FIG. 5A is a perspective view exemplary illustrating an entire plug.
Figure 5B:
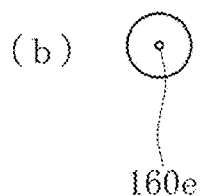
FIG. 5B is an end-face view exemplary illustrating the front face of the plug.
Figure 6A:
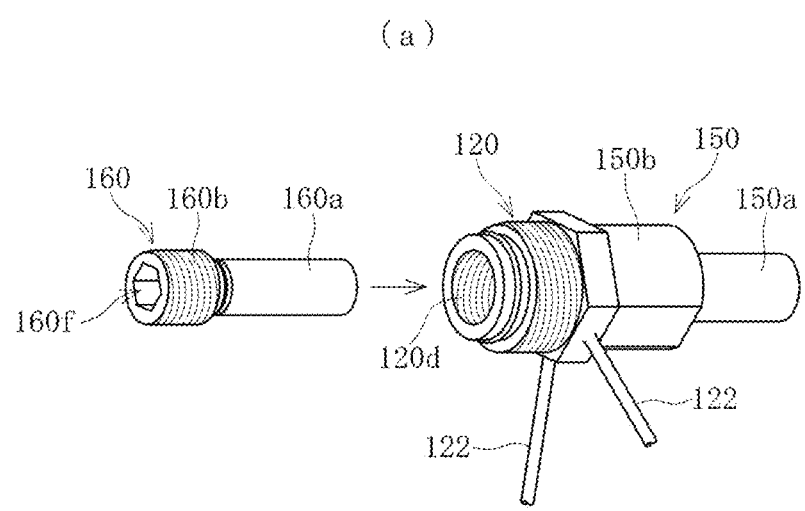
FIG. 6A is a perspective view illustrating a condition in which before the plug is screwed in the coupling member coupled to the container.
Figure 6B:
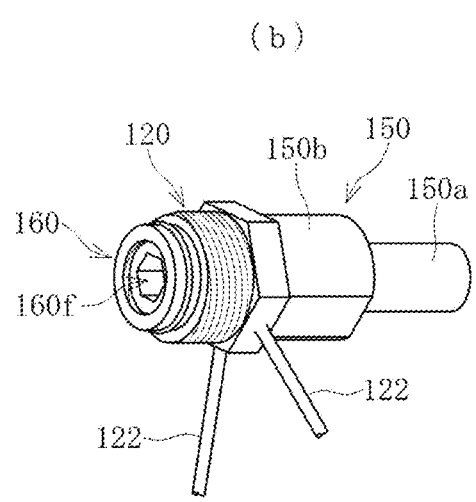
FIG. 6B is a perspective view illustrating a condition in which the plug is screwed into the end in the coupling member and is connected thereto.

The plug 160 is to seal the transferred sample 20 from the sample storing container 10 in the sample container 150. As illustrated in FIG. 5A, the plug 160 includes a columnar cylindrical plug main body 160a and a rod coupling portion 160c that has a larger diameter than that of the plug main body 160a. The plug 160 is coupled to the coupling member 120 by a male screw 160b on the outer circumference of the rod coupling portion 160c that is screwed with the female screw 120d of the coupling member 120 (see FIG. 6A), and thus the sample container 150 in which the sample 20 is placed can be sealed.

In addition, the plug 160 includes a side orifice 160d (see FIG. 5A) formed between the plug main body 160a and the rod coupling portion 160c, and a front orifice 160e (see FIGS. 5A and 5B) formed in the substantial center of the front face of the plug main body 160a. The side orifice 160d and the front orifice 160e are in communication with each other through the interior of the plug main body 160a (see FIGS. 5A and 7F), and are for keeping the sample 20 in the sample container 150 while maintaining pressure as will be explained later. In addition, a hexagon hole 160f is formed in the rear face of the rod coupling portion 160c (see FIG. 5A). By fitting the front end of the plug rod member 170 to be explained later in the hexagon hole 160f, the plug 160 can be turned in the clockwise direction, thus being coupled to the coupling member 120.

The plug rod member 170 (see FIG. 7E) is a member to couple the plug 160 to the coupling member 120. Like the sampling pipe 140, the plug rod member 170 is inserted into the cylindrical casing 130 for use. The tip of the plug rod member 170 is formed in a hexagonal shape (unillustrated), is fitted in the hexagon hole 160f in the rear end face of the plug 160 to turn and fasten the plug to the coupling member 120. A bulk head (unillustrated) like the bulk head 142 of the sampling pipe 140 is formed on the plug rod member 170 so as to produce a pressure difference between the front space 136 and the rear space 138.

According to the subsampling device 100 of this embodiment, respective materials of the flange member 110, the coupling member 120, the cylindrical casing 130, the sampling pipe 140, the plug 160 and the plug rod member 170 are stainless steel. Other materials are also applicable as long as such a material has excellent pressure tightness and corrosion resistance.

Next, an explanation will be given of a subsampling method by the subsampling device 100 from the sample 20 according to the embodiment of the present disclosure.

As illustrated in FIG. 1A, the sample storing container 10 (available from GEOTEK corporation) in which the sample 20 is placed is prepared. In order to prevent the sample 20 from being decomposed, the room temperature is set to 2° C. In addition, the ball valve 14 provided for the sample storing container 10 is closed, and the internal pressure of the sample storing container 10 and the internal temperature thereof are kept at 6 MPa and 2° C., respectively.

The flange member 110 is attached to the sample storing container 10. Next, the front male screw 120a of the coupling member 120 is screwed with the female screw (unillustrated) of the through hole 114 of the flange member 110, thereby attaching the coupling member 120 to the flange member 110. Next, the female screw (unillustrated) at the front end of the cylindrical casing 130 is screwed with the rear male screw 120b of the coupling member 120, thereby attaching the cylindrical casing 130 to the coupling member 120. At this time, the ball valve 134 is kept closed. Subsequently, the sampling pipe 140 is inserted into the internal space 135 of the cylindrical casing 130. At this time, the position is adjusted in such a way that the collecting blade 144 located at the tip of the sampling pipe 140 is located ahead of the ball valve 134 (see FIG. 1A). Thereafter, the ball valve 134 is opened, and using the syringe pump (pressure adjusting mechanism) connected to the first piping paths 112, the pressure of the interior space of the rear side of the ball valve 134, the pressure of the interior space of the flange member 110 and the coupling member 120, and the pressure of the front space 136 in the cylindrical casing 130 are adjusted to 6 MPa which is the same as the internal pressure of the sample storing container 10 by water pressure.

The ball valve 14 of the sample storing container 10 is opened, and using the syringe pump (pressure adjusting mechanism) connected to the first piping paths 112, the pressure of the front space 136 in the cylindrical casing 130 is kept to 6 MPa by water pressure. An example pressure adjusting device applicable is a syringe pump (ISCO 500D) available from ISCO corporation which is capable of drawing a fluid at 200 mL/min at maximum, and which is capable of performing a constant pressure control. By keeping the internal pressure to 6 MPa, the decomposition of the sample 20 is preventable.

Using the syringe pump connected to the second piping paths 132, the pressure of the rear space 138 in the cylindrical casing 130 is increased up to 9 MPa by water pressure. This produces a pressure difference between the front space 136 and the rear space 138, and the bulk head 142 of the sampling pipe 140 is actuated in the forward direction of the subsampling device 100 so as to reduce the volume of the front space 136 that has a low pressure (6 MPa) and to increase the volume of the rear space 138 that has a high pressure (9 MPa). By utilizing this actuation in the forward direction, and by operating the handle 146, the sampling pipe 140 is actuated in the forward direction of the subsampling device 100 (FIG. 1B) while being turned.

When the collecting blade 144 formed at the tip of the sampling pipe 140 contacts a hard sample 20 like a solidified sandstone sample, the pressure of the rear space 138 increases. When the pressure of the rear space 138 increases, a reading value by a pressure gauge 133 of the syringe pump connected to the second piping paths 132 increases. A contact of the collecting blade 144 to the sample 20 can be checked on the basis of the increase of the reading value of the pressure gauge 133. After the contact of the collecting blade 144 to the sample 20 is checked, using a weight (unillustrated) attached to the handle 146, a slight shock is applied to the sampling pipe 140, thereby causing the collecting blade 144 to bite into the sample 20. Note that the collecting blade 144 enters in the horizontal direction from the side face of the sample that is not covered by a liner 30. When the collecting blade 144 enters the interior of the sample 20, the volume of the rear space 138 increases, while the pressure of the rear space 138 decreases. Next, pressurization by the syringe pump connected to the second piping paths 132 is performed again so as to cause the pressure of the rear space 138 to be 9 MPa, and by operating the handle 146, the sampling pipe 140 is actuated in the forward direction of the subsampling device 100 while being turned. Such actions are repeated, thereby causing the sample 20 to be housed in the tip of the sampling pipe 140.

When the action of housing the sample 20 is completed, using the syringe pump connected to the second piping paths 132, the pressure of the rear space 138 is reduced down to 3 MPa. This actuates the bulk head 142 of the sampling pipe 140 in the backward direction of the subsampling device 100 so as to increase the volume of the front space 136, and to decrease the volume of the rear space 138. By utilizing this actuation in the backward direction, the handle 146 is operated to actuate the sampling pipe 140 in the backward direction (see FIG. 1B). The position is adjusted in such a way that the collecting blade 144 at the tip of the sampling pipe 140 is located ahead of the ball valve 134.

Subsequently, the ball valve 134 of the cylindrical casing 130 and the ball valve 14 of the storing container 10 are closed. At this time, since the pressure of the front space 136 in the cylindrical casing 130 is still maintained at 6 MPa, a decomposition of the sample 20 housed in the collecting blade 144 can be prevented.

Next, as illustrated in each of FIGS. 7A to 7E, the work of transferring the sample 20 having undergone the subsampling to the sample container 150 is carried out.

Figure 7A:
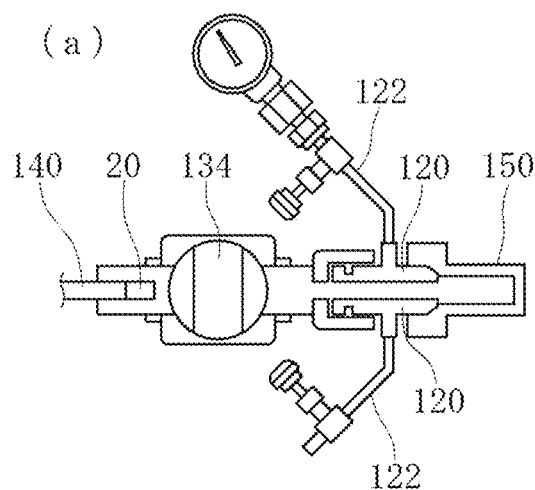
FIGS. 7A to 7F are each an operational state diagram illustrating each state of sample subsampling through operations of the ball valve, sampling pipe or plug rod member.

As illustrated in FIG. 7A, the flange member 110 and the sample storing container 10 are taken out from the coupling member 120, and the female screw 150c of the sample container 150 is screwed with the front male screw 120a of the coupling member 120 (see FIG. 4B), and thus the sample container 150 is attached to the coupling member 120. Next, using the syringe pump connected to the third pipes 122 of the coupling member 120, the internal pressure is increased up to 6 MPa and is maintained at a constant that is 6 MPa.

Figure 7B:
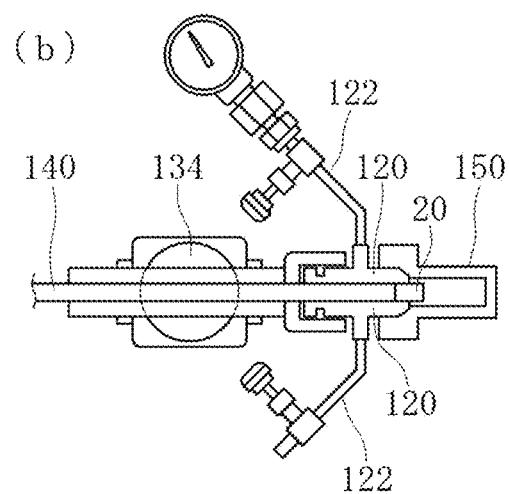
Figure 7C:
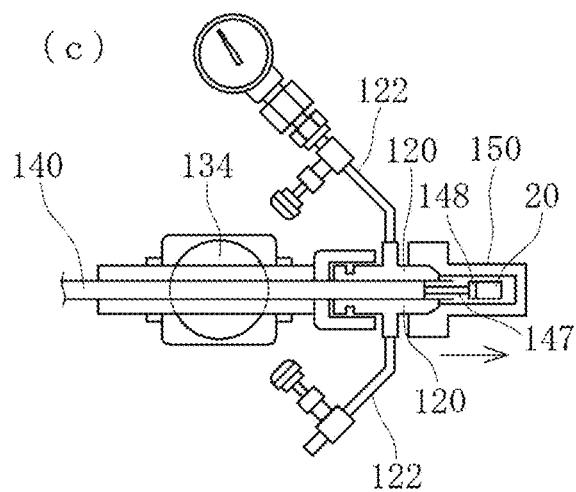
Figure 7D:
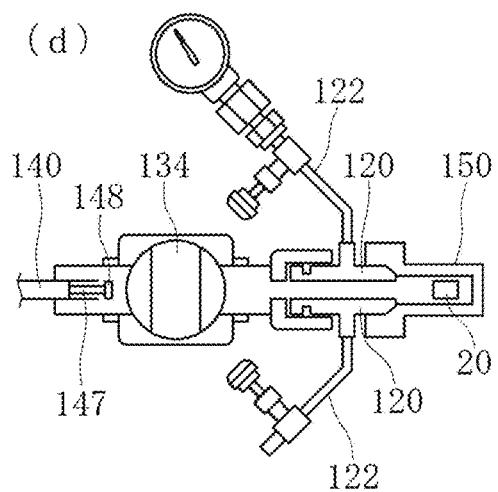

Next, as illustrated in FIG. 7B, the ball valve 134 is opened. Subsequently, using the syringe pump connected to the second piping paths 132, the pressure of the rear space 138 in the cylindrical casing 130 is increased up to 9 MPa, and like the action explained above, the sampling pipe 140 is actuated in the forward direction. When the tip of the sampling pipe 140 reaches the nearby location to the tip of the coupling member 120, as illustrated in FIG. 7C, the push-out handle 149 is operated to actuate the push-out member 148 in the forward direction, thereby pushing out the sample 20 into the sample container 150. As for the dimension of the sample pushed out into the sample container 150, the diameter is 15 mm and the length is 20 mm. Subsequently, using the syringe pump connected to the second piping paths 132, the pressure of the rear space 138 is reduced down to 3 MPa, and like the action explained above, the sampling pipe 140 is actuated in the backward direction. As illustrated in FIG. 7D, after the tip of the sampling pipe 140 is returned so as to be located behind the ball valve 134, the ball valve 134 is closed.

Next, the sampling pipe 140 in the cylindrical casing 130 is replaced with the plug rod member 170. With the ball valve 134 being closed, the sampling pipe 140 is drawn out from the cylindrical casing 130, and the plug rod member 170 that has the plug 160 fitted to the tip is inserted into the cylindrical casing 130.

Figure 7E:
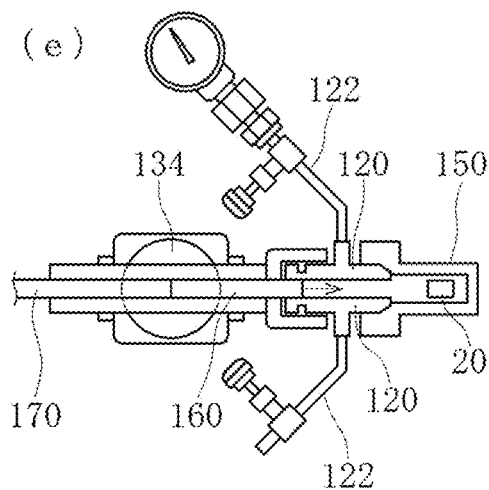
Figure 7F:
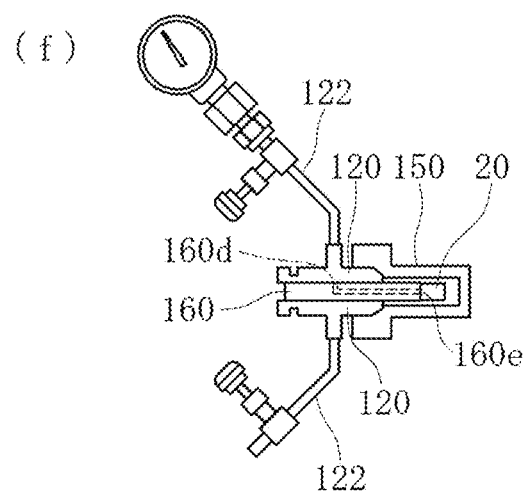

Using the syringe pump connected to the third pipes 122 of the coupling member 120, the ball valve 134 is slowly opened while the internal pressure of the sample container 150 is maintained at 6 MPa, the pressure of the front space 136 in the cylindrical casing 130 is increased up to 6 MPa, and is maintained at constant that is 6 MPa. Using the syringe pump connected to the second piping paths 132, the pressure of the rear space 138 in the cylindrical casing 130 is increased up to 9 MPa, and as illustrated in FIG. 7E, like the action explained above, the plug rod member 170 is actuated in the forward direction. The plug rod member 170 is turned in the clockwise direction, and as illustrated in FIG. 7F, the male screw 160b of the plug 160 is screwed with the female screw 120d of the coupling member 120 (see FIG. 6B). This fastens the plug 160 to the coupling member 120, thereby sealing the sample 20 in the sample container 150. Subsequently, the cylindrical casing 130 and the plug rod member 170 are taken out from the coupling member 120, and thus a transfer of the sample to the sample container 150 is completed. In the condition illustrated in FIG. 7F, the sample is ready for an X-ray CT image measurement.

As explained above, the plug 160 has, in the plug main body 160a, the side orifice 160d in communication with the front orifice 160e (see FIGS. 5A, 7F). As illustrated in FIG. 7F, using the syringe pump connected to the third pipes 122, the internal pressure of the sample container 150 can be maintained at a constant through the front orifice 160e and the side orifice 160d, and thus a decomposition of the sample 20 in the sample container 150 can be prevented.

As explained above, by utilizing the subsampling device 100 according to the embodiment of the present disclosure, subsampling is enabled on the sample like gas hydrate deposits stored in the sample storing container while maintaining the predetermined pressure. Hence, a decomposition of the sample at the time of subsampling can be prevented. In addition, the sample having undergone the subsampling can be transferred from the sample storing container to a container for analysis while the predetermined pressure is maintained, and can be provided for analysis while a decomposition of the sample is prevented. Accordingly, the amount of resources that are gas hydrate deposits, the gas productivity, and the like can be highly precisely evaluated, and the highly precise evaluation on the amount of resources is enabled using a logging tool in comparison with various typical geological layer logging tools. In addition, by separating a CT image on the basis of the brightness, the porosity, the gas hydrate saturation factor (the rate of occupying gas hydrate in pores), and the like can be obtained.

Still further, by utilizing the subsampling device 100 according to the embodiment of the present disclosure, the sample that is the gas hydrate deposits can be transferred to the container for subsampling and analysis without a need for freezing the sample, and thus a change in layout of sands can be suppressed, enabling an analysis with the layout of sands being originally present in the geological layer. In addition, an in situ analysis on sandy deposit samples is also enabled.

Yet still further, since a sample piece can be produced using the subsampling device 100 according to the embodiment of the present disclosure that performs subsampling on the sample of the gas hydrate deposits, the state of gas hydrate present in gaps among fine sand particles that are in micro order in deposits can be evaluated, enabling a more precise analysis. In addition, since the sample piece can be produced, the size of the container for analysis can be downsized, enabling various types of analysis.

The present disclosure is not limited to the above embodiment, and various changes and modifications can be made thereto. For example, in the above embodiment, the explanation has been given of a case in which, with the ball valve 14 of the sample storing container 10 being opened, and the ball valve 134 of the cylindrical casing 130 being closed, the interior is pressurized using the syringe pump (pressure adjusting mechanism) connected to the first piping paths 112. However, the pressurization may be performed with both of the ball valve 14 of the sample storing container 10 and the ball valve 134 of the cylindrical casing 130 being opened.

In addition, according to the above embodiment, the explanation has been given of a case in which a pressure difference that is 3 MPa is produced between the front space 136 and the rear space 138 to actuate the sampling pipe 140 or the plug rod member 170 in the forward direction, but this pressure difference can be changed as needed in accordance with the condition of the sample, the entire length of the cylindrical casing 130, and the like. Still further, the pressure difference may be set to zero, and the sampling pipe 140 or the plug rod member 170 may be mechanically actuated in the forward direction by, for example, an electric motor.

Yet still further, according to the above embodiment, the explanation has been given of a case in which, as for the dimension of the sample having undergone subsampling, the diameter is 15 mm and the length is 20 mm, but the dimension of the sample can be changed as needed by adjusting the diameter of the tip of the sampling pipe 140, the length of the sample to be entered in the tip of the sampling pipe 140 in the horizontal direction, and the like, in accordance with the volume of the sample container 150, and the analysis method of the sample, and the like.

According to the above embodiment, the explanation has been given of a case in which the sample container 150 which is formed of duralumin AA2024 and which has the thickness of 1.5 mm is applied, but the material of the container and the thickness thereof can be changed in accordance with the X-ray intensity of an applied X-ray CT and a normal pressure.

In the above embodiment, the explanation has been given of a case in which the container for a CT to measure the porosity is applied, but by applying a container provided with an optical window like sapphire, gas hydrate in deposits can be analyzed through Raman spectroscopy, or the like, and the occupancy of guest molecules contained in the basket of gas hydrate can be measured through in situ analysis or the like.

According to the above embodiment, when sealing by the plug 160 is accomplished, the explanation has been given of a case in which the sampling pipe 140 is replaced with the plug rod member 170, but the tip (including the collecting blade 144) of the sampling pipe 140 may be replaced with a member to screw the plug 160 (for example, a member with a tip formed in a shape that can be fitted in the hexagon hole 160f).

In the above embodiment, the explanation has been given of a case in which the syringe pump is applied as the pressure adjusting mechanism, but a pressure adjusting mechanism that can maintain pressure by water pressure or gas pressure is also applicable as appropriate.

According to the above embodiment, the explanation has been given of a case in which the subsampling is performed under conditions that are as follows: the room temperature of 2° C., the internal pressure of the front space 136 or the like which is 6 MPa, and the pressure of the rear space 138 when the sampling pipe 140 or the plug rod member 170 is actuated in the forward direction which is 9 MPa, but the temperature and the pressure can be set within a range that can suppress a decomposition of the sample.

In addition, when the internal pressure of the subsampling device 100 increases excessively, a breakup of the sample is a concern. Hence, in order to suppress an excessive pressurization applied to the sample, for example, the second piping paths 132 may be provided with a relief valve.

Still further, according to this embodiment, the explanation has been given of a case in which the conventionally well-known sample storing container available from GEOTEK corporation is applied, but various types of sample storing containers are applicable as long as the sample can be kept appropriately. Yet still further, the diameter of the through hole 114 in the flange member 110 can be changed as needed in accordance with the type of the sample storing container.

According to the above embodiment, the explanation has been given of a case in which the sampling pipe 140 is actuated by a manual operation given to the handle 146, but the sampling pipe 140 may be actuated by, for example, an electric motor.

In the above embodiment, although the explanation has been given of a case in which a contact of the collecting blade 144 to the sample 20 is checked on the basis of the increase in reading value of the pressure gauge 133 of the syringe pump, this check work may also be accomplished by measuring how much the sampling pipe 140 is pushed in the forward direction. In addition, as explained above, when the sampling pipe 140 is actuated by an electric motor, the contact can be checked by measuring a load value or the like to the motor.

Still further, according to the above embodiment, the explanation has been given of a case in which the sample 20 is sealed in the sample container 150 using the screw-in type plug 160, but the sealing action may be accomplished by, for example, thermal bonding of a plug to the sample container 150.

EXAMPLE

Subsampling was performed on a sample of simulated gas hydrate deposits, and the sample was transferred from a sample storing container to a sample container for analysis.

As explained above (see FIGS. 1A to 7F), subsampling was performed on the sample 20, and the sample was transferred from the sample storing container 10 to the sample container 150. However, the sequential subsampling works were carried out under conditions in which the room temperature was 5° C., the internal pressure of the front space 136 and that of the sample container 150, and the like were 3 MPa, the pressure of the rear space 138 when the sampling pipe 140 or the plug rod member 170 was actuated in the forward direction was 6 MPa, and the pressure of the rear space 138 when those were actuated in the backward direction was 2 MPa.

As for the simulated gas hydrate deposits, hydrous sands obtained by mixing and stirring MIKAWA silica sands No. 6 of 160 g with water 40 g were artificially produced by gas permeation method, and were taken as the sample 20. With the ball valve 14 of the sample storing container 10 (available from GEOTEK corporation) being opened and the ball valve 134 of the cylindrical casing 130 being opened, a xenon gas was charged via the first piping paths 112, this condition was left for 24 hours, and the sample 20 was created in the sample storing container 10. The reason why the xenon gas was applied in this example is because xenon serves as the contrast media for gas hydrate when an observation by an X-ray CT is carried out since xenon has a high X-ray absorption coefficient.

Figure 8A:
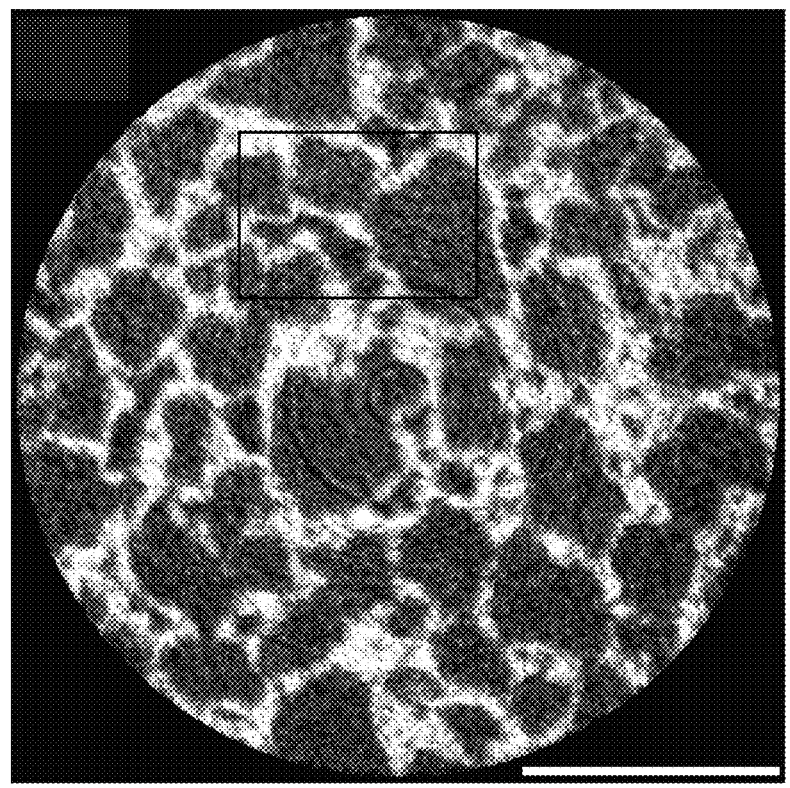
FIG. 8A is a diagram that is an X-ray CT image of a gas hydrate deposit sample having undergone subsampling in an example of the present disclosure.
Figure 8B:
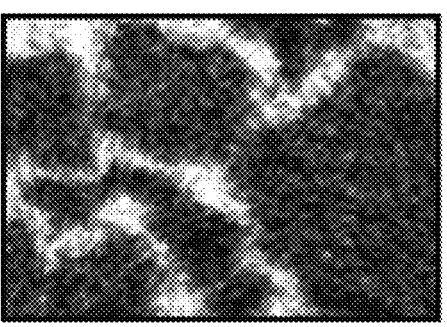
FIG. 8B is a diagram illustrating the area within the black frame in FIG. 8A in an enlarged manner.
Figure 8C:
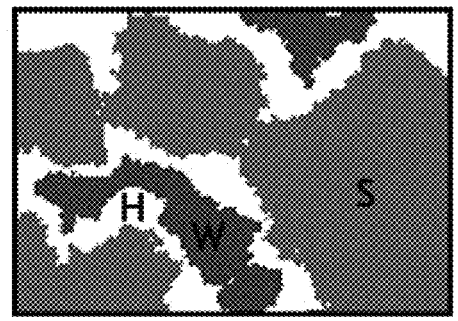
FIG. 8C is a diagram illustrating FIG. 8B in a color-coded manner on the basis of a difference in brightness.

In the first example, the X-ray CT image of the sample having undergone subsampling was measured. FIG. 8A shows a two-dimensional cross-sectional CT image. Since the subsampling was performed while the pressure was maintained without causing gas hydrate to be decomposed, the gas hydrate (white area in FIG. 8A) present in pores was confirmed. In addition, FIG. 8B is an enlarged black frame in FIG. 8A, and FIG. 8C is color-coded FIG. 8B on the basis of the difference in brightness. The symbol S in FIG. 8C indicates the sand particles of the applied MIKAWA silica sands No. 6, the symbol H indicates the gas hydrate, and the symbol W indicates water. In view of FIG. 8C, the porosity of the gas hydrate deposits having undergone subsampling which was 39.1%, and the gas hydrate saturation factor which was 85.1% were obtained.

The foregoing describes some example embodiments for explanatory purposes. Although the foregoing discussion has presented specific embodiments, persons skilled in the art will recognize that changes may be made in form and detail without departing from the broader spirit and scope of the invention. Accordingly, the specification and drawings are to be regarded in an illustrative rather than a restrictive sense. This detailed description, therefore, is not to be taken in a limiting sense, and the scope of the invention is defined only by the included claims, along with the full range of equivalents to which such claims are entitled.

This application is based on Japanese Patent Application No. 2013-254505 filed on Dec. 9, 2013. The entire specification, claims, and drawings of Japanese Patent Application No. 2013-254505 are herein incorporated in this specification by reference.

INDUSTRIAL APPLICABILITY

According to the subsampling device 100 of the embodiment of the present disclosure, a highly precise evaluation of the amount of resources, the gas productivity, and the like is enabled. Consequently, a selection of the optimized gas hydrate reservoir and a highly efficient gas production from the gas hydrate layer are enabled, thereby remarkably reducing natural gas production costs. In addition, a development of the optimized logging tool for gas hydrate deposit layers is also enabled.

REFERENCE SIGNS LIST

10 Sample storing container
11 Housing space
14 Ball valve
20 Sample
30 Liner
100 Subsampling device
110 Flange member
112 First piping path
114 Through hole
120 Coupling member
120a Front male screw
120b Rear male screw
120c Cavity
120d Female screw
120e Center flange
122 Third pipe
130 Cylindrical casing
132 Second piping path
133 Pressure gauge
134 Ball valve
135 Internal space
136 Front space
138 Rear space
140 Sampling pipe
142 Bulk head
144 Collecting blade
146 Handle
147 Shaft member
148 Push-out member
149 Push-out handle
150 Sample container
150a Keeper portion
150b Coupler portion
150c Female screw 160 Plug
160a Plug main body
160b Male screw
160c Rod coupling member
160d Side orifice
160e Front orifice
160f Hexagon hole
170 Plug rod member

The invention claimed is:

1. A subsampling device comprising:
    a flange member in which a through hole to be in communication with a housing space of a sample storing container is formed, and which is formed with at least one first pressure adjusting passage in communication with the through hole, and which is coupled to a rear end face of the sample storing container;
    a coupling member in which a cavity to be in communication with the through hole of the flange member is formed, and which has a first end coupled to the through hole of the flange member, wherein the flange member is removable from the first end of the coupling member;
    a cylindrical casing which has a front end connected to a second end of the coupling member, comprises a ball valve disposed at a nearby location to the front end, and formed with at least one second pressure adjusting passage formed at a nearby location to a rear end of the cylindrical casing and in communication with an internal space thereof;
    a sampling pipe which is provided with a partition wall that divides the internal space into a front space and a rear space, comprises a collecting blade formed at a front end, and slides in the internal space of the cylindrical casing; and
    a sample container which is connected to the first end of the coupling member after the flange member is removed from the first end of the coupling member,
    wherein the sliding sampling pipe causes the collecting blade to contact a sample in the sample storing container to perform subsampling on the sample so as to be held at the front end of the sampling pipe, and the sample having undergone the subsampling is stored in the attached sample container replaced with the flange member.

2. The subsampling device according to claim 1, wherein the sampling pipe slides by a pressure difference between the front space and the rear space.

3. The subsampling device according to claim 1, wherein the coupling member comprises at least one third pressure adjusting passage in communication with the cavity.

4. The subsampling device according to claim 1, wherein the second pressure adjusting passage is connected to an external pressure adjusting mechanism and produces the pressure difference between the front space and the rear space by the pressure adjusting mechanism.

5. The subsampling device according to claim 1, further comprising a push-out member which protrudes from the front end of the sampling pipe, and which causes the sample to be housed in the sample container.

6. The subsampling device according to claim 1, wherein an open end of the sample container is sealed after the sample is housed therein.

7. A subsampling method for a sample with the subsampling device of claim 1 comprising:
    causing the sampling pipe to slide along an axial line direction by a pressure difference between a front space and a rear space relative to the sampling pipe, causing the collecting blade of the sampling pipe to contact the sample in the sample storing container to collect the sample;
    taking out the sample storing container and the flange member from the coupling member and attaching a sample container to the coupling member;
    housing the collected sample held at a tip of the sampling pipe in the sample container; and
    sealing an open end of the sample container housing therein the sample.

* * * * *